United States Patent
Hansen et al.

(10) Patent No.: US 10,047,379 B2
(45) Date of Patent: *Aug. 14, 2018

(54) METHOD FOR THE SIMULTANEOUS PRODUCTION OF ETHANOL AND A FERMENTED, SOLID PRODUCT

(71) Applicant: Hamlet Protein A/S, Horsens (DK)

(72) Inventors: Ole Kaae Hansen, Egå (DK); Katrine Hvid Ellegård, Ry (DK); Karl Kristian Thomsen, Horsens (DK)

(73) Assignee: HAMLET PROTEIN A/S, Horsens (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/345,725

(22) Filed: Nov. 8, 2016

(65) Prior Publication Data

US 2017/0233767 A1 Aug. 17, 2017

Related U.S. Application Data

(63) Continuation of application No. 14/349,170, filed as application No. PCT/EP2012/069601 on Oct. 4, 2012, now Pat. No. 9,528,128.

(60) Provisional application No. 61/543,907, filed on Oct. 6, 2011, provisional application No. 61/638,777, filed on Apr. 26, 2012.

(30) Foreign Application Priority Data

Oct. 6, 2011 (EP) .................................. 11184135

(51) Int. Cl.
| | |
|---|---|
| C12P 7/06 | (2006.01) |
| C12P 21/00 | (2006.01) |
| A23K 10/12 | (2016.01) |
| A23L 33/185 | (2016.01) |

(52) U.S. Cl.
CPC ............... *C12P 7/06* (2013.01); *A23K 10/12* (2016.05); *A23L 33/185* (2016.08); *C12P 21/00* (2013.01); *C12Y 302/01* (2013.01); *C12Y 302/01001* (2013.01); *C12Y 302/01003* (2013.01); *C12Y 302/01022* (2013.01); *A23V 2002/00* (2013.01)

(58) Field of Classification Search
None
See application file for complete search history.

(56) References Cited

U.S. PATENT DOCUMENTS

| | | |
|---|---|---|
| 3,451,821 A | 6/1969 | Todd |
| 9,528,128 B2 | 12/2016 | Hansen et al. |
| 2014/0212543 A1 | 7/2014 | Lywood et al. |

FOREIGN PATENT DOCUMENTS

| | | |
|---|---|---|
| EP | 1 355 533 B1 | 10/2005 |
| GB | 2 049 457 A | 12/1980 |
| WO | WO 02/17726 A2 | 3/2002 |
| WO | WO 2004/113490 A2 | 12/2004 |
| WO | WO 2005/06980 A2 | 8/2005 |
| WO | WO 2006/056838 | 6/2006 |
| WO | WO 2006/102907 A1 | 10/2006 |
| WO | WO 2006/113683 A2 | 10/2006 |
| WO | WO-2007/036795 A1 | 4/2007 |
| WO | WO 2008/076747 A2 | 6/2008 |
| WO | WO 2009/129320 | 10/2009 |
| WO | WO 2009/143591 A2 | 12/2009 |
| WO | WO 2010/096673 A1 | 8/2010 |
| WO | WO 2011/147923 A1 | 12/2011 |
| WO | WO-2012/140444 A1 | 10/2012 |

OTHER PUBLICATIONS

International Search Report dated Dec. 10, 2012 in application No. PCT/EP2012/069601.
Gibbons et al., "A Continuous, Farm-Scale, Solid-Phase Fermentation Process for Fuel Ethanol and Protein Feed Production from Fodder Beets," Biotechnology and Bioengineering, vol. 26, pp. 1098-1197, Sep. 1984.
Office Action dated Aug. 14, 2015 in U.S. Appl. No. 14/349,170 (now U.S. Pat. No. 9,528,128).
Office Action dated Dec. 3, 2015 in U.S. Appl. No. 14/349,170 (now U.S. Pat. No. 9,528,128).

(Continued)

*Primary Examiner* — Suzanne M Noakes
*Assistant Examiner* — Stephen M Chong
(74) *Attorney, Agent, or Firm* — Foley & Lardner LLP

(57) ABSTRACT

The invention relates to a method for the simultaneous production of a fermented, solid product and ethanol comprising the following steps: 1) providing a mixture of milled or flaked or otherwise disintegrated biomass, comprising oligosaccharides and/or polysaccharides and live yeast in a dry matter ratio of from 2:1 to 100:1, and water; 2) fermenting the mixture resulting from step (1) under conditions where the water content in the initial mixture does not exceed 65% by weight, for 1-36 hours at a temperature of about 25-60° C. under anaerobic conditions; 3) incubating the fermented mixture resulting from step (2) for 0.5-240 minutes at a temperature of about 70-150° C.; and 4) separating wet fermented, solid product from the fermented mixture resulting from step (3); further comprising either a) that the fermentation in step (2) is performed in one or more interconnected paddle worm or continuous worm conveyers with inlet means for the fermentation mixture and additives and outlet means for the ferment as well as control means for rotation speed, temperature and pH, or b) that one or more processing aids are added in any of steps (1), (2) and (3) and further comprising a step of 5) separating crude ethanol from the fermented mixture in step (2) by vacuum and/or in step (3) by vacuum or by injection of steam and condensing the surplus stripping steam. The invention further relates to the products of this method as well as uses thereof.

21 Claims, No Drawings

(56) References Cited

OTHER PUBLICATIONS

Office Action dated Apr. 28, 2016 in U.S. Appl. No. 14/349,170 (now U.S. Pat. No. 9,528,128).
Notice of Allowance dated Aug. 9, 2016 in U.S. Appl. No. 14/349,170 (now U.S. Pat. No. 9,528,128).

METHOD FOR THE SIMULTANEOUS PRODUCTION OF ETHANOL AND A FERMENTED, SOLID PRODUCT

FIELD OF THE INVENTION

The present invention relates to a method for the simultaneous production of a fermented, solid product and ethanol.

Furthermore it relates to the products obtainable by the method as well as the use of the products obtained.

BACKGROUND OF THE INVENTION

There is a need for development of sustainable energy sources, and bio ethanol is an attractive source as fuel for transportation. Therefore, there is a need for a process that can produce bio ethanol at a low cost. There is further a need for providing alternative sources of protein for human food and animal feed.

The ability of yeast to convert simple sugars into ethanol is well known. The conversion process is frequently performed by milling a starch-containing raw material and converting the starch into fermentable sugars by enzymatic or acid hydrolysis. After this, yeast is added to ferment the sugars to alcohol and carbon dioxide.

This process is usually performed at low dry matter content in a batch or fed-batch or a continuous process with water content of 90% or more. In 2nd generation production of bio ethanol the dry matter in the fermentation broth is reported to be up to approx. 20%. After fermentation the alcohol is distilled off.

From an economic point of view the high water content in the process is undesirable for the following reasons: High processing costs and high investment costs due to the large volume of the reaction vessels.

WO 2005/069840 A2 discloses a process for producing a fermentation product, such as ethanol, from milled starch-containing material comprising saccharifying the milled starch-containing material with a specially derived glucoamylase without gelatinization of said starch-containing material and fermenting using a fermenting microorganism.

WO 2006/102907 A1 discloses a method of preparing a fermented protein product derived from yeast and proteinaceous pulse parts by fermenting under anaerobic conditions at water content not exceeding 80% and incubating the fermented mixture in a closed system.

WO 2004/113490 A3 discloses a method for the directed, selective solid-phase culturing of stable microbial mixed populations for the continuous preparation of defined enzyme and metabolite mixtures and a suitable bioreactor therefore.

WO2006/129320 A2 discloses a method of producing a protein concentrate from starch containing grain which method comprises fermentation, and wherein the fermentation product can be ethanol.

WO 2006/113683 A2 discloses a method for the production of ethanol and a modified animal feed by saccharification and fermentation.

WO2006/056838 A1 discloses a process for liquefaction and saccharification of polysaccharide containing biomasses having a dry matter content of above 20%, which method comprises enzymatic hydrolysis combined with mixing by a gravity based type of mixing providing mechanical processing. The resulting processed biomass of the process may be further utilized for ethanol production in a subsequent fermentation process.

WO 2007/036795 A1 discloses a process for production of fermentation products, including bioethanol by pretreatment and enzymatic hydrolysis fermentation of waste fractions containing mono- and/or polysaccharides, having a dry matter content of above 20% using free fall mixing for the mechanical processing of the waste fraction and subsequent fermentation.

A fermentor for processing a raw material and an operational method therefore is disclosed in EP 1 355 533 B1; the fermentor disclosed is for continuous processing of a product mixture, particularly dough, or a mixture of water and ground cereal products. A vertical reactor for continuous fermentation utilizing an Archimedean screw is disclosed in GB 2 049 457 A.

The object of the present invention is to provide an improved method for the production of bio ethanol allowing simultaneous production of a valuable fermented, solid product, where the water content during the process is low.

Another object is to provide a process, which can be performed at low costs due to the low water content and equipment of low investment and thereby also provide the products at lower costs.

Yet another object is to provide a fermented, solid product of high commercial value.

These objects are fulfilled with the process and the products of the present invention.

SUMMARY OF THE INVENTION

Accordingly, in one aspect the present invention relates to a method for the simultaneous production of a fermented, solid product and ethanol comprising the following steps:

1) providing a mixture of milled or flaked or otherwise disintegrated biomass, comprising oligosaccharides and/or polysaccharides and live yeast in a dry matter ratio of from 2:1 to 100:1, and water;
2) fermenting the mixture resulting from step (1) under conditions where the water content in the initial mixture does not exceed 65% by weight, for 1-36 hours at a temperature of about 25-60° C. under anaerobic conditions;
3) incubating the fermented mixture resulting from step (2) for 0.5-240 minutes at a temperature of about 70-150° C.; and
4) separating wet fermented, solid product from the fermented mixture resulting from step (3);

further comprising that the fermentation in step (2) is performed in one or more interconnected paddle worm or continuous worm conveyers, optionally arranged non-vertically, with inlet means for the fermentation mixture and additives and outlet means for the ferment as well as control means for rotation speed, temperature and pH, and further comprising a step of 5) separating crude ethanol from the fermented mixture in step (2) by vacuum and/or in step (3) by vacuum or by injection of steam and condensing the surplus stripping steam.

In a second aspect the invention relates to a method for the simultaneous production of a fermented, solid product and ethanol comprising the following steps:

1) providing a mixture of milled or flaked or otherwise disintegrated biomass, comprising oligosaccharides and/or polysaccharides and live yeast in a dry matter ratio of from 2:1 to 100:1, and water;
2) fermenting the mixture resulting from step (1) under conditions where the water content in the initial mixture does not exceed 65% by weight, for 1-36 hours at a temperature of about 25-60° C. under anaerobic conditions;

3) incubating the fermented mixture resulting from step (2) for 0.5-240 minutes at a temperature of about 70-150° C.; and 4) separating wet fermented, solid product from the fermented mixture resulting from step (3);

further comprising that one or more processing aids are added in any of steps (1), (2) and (3), and further comprising a step of 5) separating crude ethanol from the fermented mixture in step (2) by vacuum and/or in step (3) by vacuum or by injection of steam and condensing the surplus stripping steam.

It is surprising that by the combination according to the first aspect of the invention of two special measures in the method, viz. firstly, performing the fermentation step (2) in one or more interconnected paddle worm or continuous worm conveyers and, secondly, separating the crude ethanol from the fermentation mixture already in step (2) by vacuum and/or in step (3) by vacuum or by injection of steam and condensing the surplus stripping steam, it is possible to conduct the method for producing ethanol at a substantially higher dry matter content than in the prior art methods and simultaneously to produce a valuable fermented, solid biological product.

It is further surprising that by applying the second aspect of the invention of firstly, adding one or more processing aids, such as one or more enzymes or one or more plant based components, and, secondly, separating the crude ethanol from the fermentation mixture already in step (2) by vacuum and/or in step (3) by vacuum or by injection of steam and condensing the surplus stripping steam, it is likewise possible to conduct the method for producing ethanol at a substantially higher dry matter content than in the prior art methods and simultaneously to produce a valuable fermented, solid biological product.

Normally, when the water content is reduced, and thereby the dry matter content of the mixture to be fermented is high, a fermentation mixture tends to compact so that the transportation behavior is affected negatively, and at certain water content the mixture is compacted to an extent so that the transportation is stopped.

The water content may be further reduced to 60%, 55%, 50% or 45% or even to 40% without seriously affecting the conversion of oligosaccharides to fermentable sugars or the subsequent fermentation of those sugars. The production of the same amount of alcohol in a reduced amount of water leads to a higher concentration of alcohol in the product.

The method of the invention in its first aspect makes use of a special fermentor constructed so that besides transportation the conveyers also provide mixing and lifting of the material. This makes it possible to perform the fermentation in a mixture where the water content initially does not exceed 65% by weight i.e. the fermentation mixture has a content of dry matter of 35% by weight or more in the initial fermentation mixture at the beginning of the process, whereas the dry matter content in similar prior art methods are about 20% or lower. Due to the low water content and the possibility of separating crude ethanol in an early stage of the process, the process can be performed at lower costs than prior art methods. The method of the invention in its second aspect in one embodiment also makes use of said special fermentor.

In one embodiment of the invention said continuous worm conveyer is an optionally modified type of a single bladed or multi bladed Archimedean screw or intersected screw designed to transport the fermenting mixture and at the same time lifting the material so that it is transported and agitated without compacting it, and in one aspect is non-vertical.

In another embodiment of the invention said special fermentor is a vertical screw mixer, e.g. a Nauta Mixer.

Normally more than 90% by weight of the ethanol produced can be extracted. The yield of ethanol is dependent upon the content of carbohydrates in the fermentation mixture and the conversion into fermentable sugars. On the basis of defatted soy it is possible to generate 4-5% by weight of ethanol, whereas on wheat approx. 20% by weight can be obtained.

The invention further provides a crude ethanol obtainable by a process according to the invention and further comprising small amounts of components resulting from the fermented biomass, e.g. 0.01-1% of other alcohols and ethers, such as ethyl acetate, 3-methyl-1-butanol and/or 2-methyl-1-butanol, and a fermented, solid product obtainable by a process according to the invention comprising proteins, carbohydrates and optionally dietary fibers and/or salts resulting from the fermented biomass, wherein yeast protein is comprised in an amount of 1-95% by weight on dry matter basis, and carbohydrate is comprised in an amount of 5-99% by weight on dry matter basis.

Definitions

In the context of the current invention, the following terms are meant to comprise the following, unless defined elsewhere in the description.

The terms "about", "around", "approximately", or "~" are meant to indicate e.g. the measuring uncertainty commonly experienced in the art, which can be in the order of magnitude of e.g. +/−1, 2, 5, 10, 20, or even 50%.

The term "comprising" is to be interpreted as specifying the presence of the stated part(s), step(s), feature(s), composition(s), chemical(s), or component(s), but does not exclude the presence of one or more additional parts, steps, features, compositions, chemicals or components. E.g., a composition comprising a chemical compound may thus comprise additional chemical compounds, etc.

Biomass:

Comprises biological material that can be used for fuel or as a raw material in industrial production.

In this context, biomass refers to plant matter in the form of stem, twig, leaf, flower, fruit, seed, etc.

Otherwise Disintegrated:

Means disintegrated by acid or alkaline pressure-cooking or ultrasonic treatment.

Oligosaccharides and Polysaccharides:

An oligosaccharide is a saccharide polymer containing a small number of component monomer sugars, also known as simple sugars.

Polysaccharides are saccharide polymers containing a large number of component monomer sugars, also known as complex carbohydrates. Examples include storage polysaccharides such as starch and structural polysaccharides such as cellulose.

Carbohydrates:

Comprise mono-, di-, oligo- and polysaccharides.

Proteinaceous Materials:

Comprise organic compounds made of amino acids arranged in a linear chain and joined together by a bond called a peptide bond. At a chain length of up to approximately 50 amino acids the compound is called a peptide, at higher molecular weight the organic compound is called a polypeptide or a protein.

Fats:

Comprise esters between fatty acids and glycerol. One molecule of glycerol can be esterified to one, two and tree fatty acid molecules resulting in a monoglyceride, a diglyceride or a triglyceride respectively. Usually fats consist of mainly triglycerides and minor amounts of lecithins, sterols, etc. If the fat is liquid at room temperature it is normally called oil. With respect to oils, fats and related products in this context, reference is made to "Physical and Chemical Characteristics of Oils, Fats and Waxes", AOCS, 1996, as well as "Lipid Glossary 2", F. D. Gunstone, The Oily Press, 2004.

Glycerides:

Comprise mono-, di- and triglycerides.

Processing Aids:

1. Enzymes

Enzyme(s) is a very large class of protein substances that act as catalysts. Commonly, they are divided in six classes, and the main classes falling within the scope of this invention can be transferases that transfer functional groups and the hydrolases that hydrolyze various bonds. Typical examples can comprise: protease(s), peptidase(s), (α-)galactosidase(s), amylase(s), glucanase(s), pectinase(s), hemicellulase(s), phytase(s), lipase(s), phospholipase(s) and oxido-reductase(s).

2. Plant Components and Organic Processing Agents

Some of the functional properties that are important in this context are: Antioxidant, anti-bacterial action, wetting properties and stimulation of enzymes.

The list of plant-based components is huge, but the most important are the following: Rosemary, thyme, oregano, flavonoids, phenolic acids, saponins and α- and β-acids from hops for the modulation of soluble carbohydrates, e.g. α-lupulic acid.

Furthermore organic acids e.g. Sorbic-, propionic-, lactic-, citric- and ascorbic acid and their salts for the adjustment of the pH-value, preservation and chelating properties is part of this group of processing aids.

A further member in this group is lipids for the modulation of ethanol tolerance of the yeast e.g. Cholesterol, oils and olein fractions of vegetable fats that are high in C18-unsaturated fatty acids.

3. Inorganic Processing Agents

Comprise inorganic compositions that are able to preserve the fermenting mixture against bacterial attack during processing e.g. Sodium bisulfite, etc. Anticaking and flow improving agents in the final product e.g. Potassium aluminum silicate, etc.

Processed Food Products:

Comprise dairy products, processed meat products, sweets, desserts, ice cream desserts, canned products, freeze dried meals, dressings, soups, convenience food, bread, cakes, etc.

Processed Feed Products:

Comprise ready-to-use feed for animals such as piglets, calves, poultry, furred animals, sheep, cats, dogs, fish and crustaceans, etc.

Pharmaceutical Products:

Comprise products, typically in the form of a tablet or in granulated form, containing one or more biologically active ingredients intended for curing and/or alleviating the symptoms of a disease or a condition. Pharmaceutical products furthermore comprise pharmaceutically acceptable excipients and/or carriers. The solid bio products herein disclosed are very well suited for use as a pharmaceutically acceptable ingredient in a tablet or granulate.

Cosmetic Products:

Comprise products intended for personal hygiene as well as improved appearance such as conditioners and bath preparations.

DETAILED DESCRIPTION OF THE INVENTION

In one embodiment of the method of the invention in its first aspect one or more processing aids are added in any of the steps (1), (2) and (3).

In one embodiments of the method of the inventions in its second aspect the fermentation in step (2) is performed in one or more interconnected paddle worm or continuous worm conveyers, optionally arranged vertically, with inlet means for the fermentation mixture and additives and outlet means for the ferment as well as control means for rotation speed, temperature and pH, and/or further comprising a step (5) of separating crude ethanol from the fermented mixture in step (2) by vacuum and/or in step (3) by vacuum or by injection of steam and condensing the surplus stripping steam.

In one embodiment the methods of the invention further comprise a step of 2a) fermenting the mixture resulting from step (2) for 1-36 hours at a temperature of about 25-60° C. under aerobic conditions and optionally separating crude ethanol from the fermented mixture in step (2a) by vacuum.

In another embodiment step (3) is carried out at a temperature of about 70-120° C. Generally, in the incubation step (3) a high temperature is used for short time, and lower temperatures are used for longer incubation times.

The dry matter content may vary from 35 to 70% by weight of the mixture of step 1), e.g. from 40 to 65% or from 45 to 60% or from 50 to 55%.

In embodiments of both aspects of the method of the invention the at least one processing aids added in any of steps (1), (2), (2a) and (3) is one or more enzymes, and an enzymatic saccharification process converting the oligo- and/or polysaccharides into fermentable carbohydrates takes place simultaneously with the yeast fermentation. The enzyme(s) may be selected from the group consisting of protease(s), peptidase(s), galactosidase(s), amylase(s), pectinase(s), cellulase(s), hemicellulase(s), glucanase(s), glucosidase(s), phytase(s), lipase(s), oxido-reductase(s) and phospholipase(s).

This embodiment has been found to be most advantageous from an investment point of view as well as with a view to shorten reaction time. Thus, by continuously fermenting the liberated fermentable sugars, catabolite repression is avoided and the mass balance equilibrium pushed to the right.

This is of particular importance when operating at the high dry matter content according to the invention.

In other embodiments of both aspects of the method of the invention the at least one processing aids is one or more plant-based component, such as a component selected from rosemary, thyme, oregano, flavonoids, phenolic acids, saponins and α- and β-acids from hops for the modulation of soluble carbohydrates, e.g. α-lupulic acid.

The yeast to be used in the method of the invention may e.g. be selected among *Saccharomyces cerevisiae* strains, including spent brewer's yeast and spent distiller's yeast and spent yeast from wine production, as well as yeast strains fermenting C5 sugars. C5 sugars are pentose-based sugars, such as xylose and arabinose.

In another embodiment biomass comprising oligosaccharides and/or polysaccharides further comprises proteins originating from proteinaceous plant parts, e.g. pulses, such as soy, pea, lupine, and/or cereals, such as wheat. An example of a suitable biomass is ground or flaked, defatted soybeans. A suitable biomass can also be ground or flaked cereals e.g. wheat. Furthermore, mixtures of pulse parts and cereals are suitable biomass for processing by the method.

The biomass comprising oligosaccharides and/or polysaccharides and optionally proteins may further comprise oils and fats, e.g. from seeds of oil bearing plants, e.g. rape seed. An example of a suitable biomass is ground or flaked, full fat soybeans or rapeseeds or their mixtures.

The separation of fermented product and ethanol in steps (4) and (5) may be performed by standard unit operations comprising e.g. stripping with steam, evaporation, condensation, distillation, filtration, centrifugation and sedimentation.

In other embodiments separated compounds may be subject to special treatments comprising e.g. purification, drying, milling and admixture of other ingredients. All the unit operations that can be used for this as well as for the separation in steps (4) and (5) are well known to a person skilled in the art.

The separated fermented, solid product may subsequently be made more water-soluble by hydrolysis, e.g. by enzymes.

The method of the invention may e.g. be performed as a batch, fed-batch or continuous process.

Finally, the ethanol produced by the process of the invention may be used to generate heat for the process e.g. by catalytic combustion and thus at the same time get rid of polluting volatile organic compounds, e.g. hexane. In this case the by-products generated will be carbon dioxide and water.

In one embodiment the fermented, solid product of the invention comprises protein in an amount of 25-90% by weight on dry matter basis, and glyceride in an amount of 0-30% by weight on dry matter basis. About 1-35% relative of said protein may be originating from yeast protein and about 65-99% relative of said protein may be originating from proteinaceous plant parts, e.g. from pulses and/or cereal, such as soybeans and/or wheat.

In another embodiment the fermented, solid product is derived from biomass predominantly comprising oligosaccharides and/or polysaccharides and comprises yeast protein in an amount of 1-95% by weight on dry matter basis and carbohydrate in an amount of 5-99% by weight on dry matter basis.

The crude ethanol obtainable according to the invention can be used for the generation of heat for the fermentation process.

The invention also relates to the use of a fermented, solid product according to the invention in a processed food product for human and/or animal consumption; as an ingredient to be used in a food or feed product; or as an ingredient of a cosmetic or a pharmaceutical product or a nutritional supplement.

Finally the invention relates to a food, feed, cosmetic or pharmaceutical product or a nutritional supplement containing from 1 to 99% by weight of a fermented, solid product according to the invention.

EXAMPLES

Example 1

Fermentation in a Continuous Process of a Biomass Comprising Polysaccharides and Proteins from Pulses In the following the fermentation of a biomass based on defatted soy is illustrated.

100 kg per hour of dehulled and defatted, flash desolventised soy flakes were continuously fed to a closed single bladed worm conveyer able to transport, lift and mix the material (bioreactor). At the same time water and slurry of spent brewer's yeast (10% dry matter) where added in an amount to reach a dry matter content of 40% by weight in the mixture.

In the bioreactor the resulting slurry was incubated for 8 hours at 34° C.

Next, the slurry was heated in a second incubator (bioreactor) to 100° C. with injection of a surplus of life steam for approx. 30 min. The surplus steam containing volatile organic compounds (VOC's) comprising ethanol was transferred to a cooling heat exchanger.

The resulting condensate had an ethanol concentration of 15% by weight. The ethanol yield was 4.8 kg per 100 kg of soy flakes.

Subsequently, the wet solid product was flash dried and milled at an Alpine pin mill.

The dried product had the following analysis:

| | |
|---|---|
| Crude Protein (N × 6.25) | 58.3% |
| Carbohydrates | 24.0% |
| Moisture | 5.6% |
| Crude fat | 0.9% |
| Crude fiber | 4.2% |
| Ash | 7.0% |

Furthermore, anti-nutritional factors in the dried, fermented product were significantly reduced vs. the raw material content:

| | Fermented Product | Raw Material |
|---|---|---|
| Oligosaccharides | 0.9% | 13.5% |
| Trypsin Inhibitor | 2,900 TIU/g | 62,000 TIU/g |
| β-conglycinin | 8 ppm | 90,000 ppm |

The fermented product is highly nutritious and palatable and thus suitable as an ingredient in a number of food and feed products.

Example 2

Composition of VOC's in Exhaust Drying Air of a Fermented Biomass Comprising Polysaccharides and Proteins In the following the content of volatile organic compounds (VOC's) in the drying air from a fermented biomass based on defatted soy is illustrated. An air amount of two liter was collected at a temperature of 55.7° C. and a relative humidity of 67.1% in a Tedlarbag.

Analytical Methods:

GC/FID—refers to a method where the sample from the Tedlarbag was analyzed by GC analysis and quantified vs. Ethanol using a FID detector.

GC/MS—refers to a method where the sample components from the Tedlarbag are first adsorbed in a tube containing an adsorbent material followed by desorbtion for GC analysis by heating, and quantified by the recording of peak area vs. Toluen-$d_6$. The identification was done by comparison of the mass spectra with a NIST-database.

The results are tabulated in the following:

| Component | CAS-nr | Content mg/m³ | Analytical method |
| --- | --- | --- | --- |
| Ethanol | 64-17-5 | 1,300 | GC/FID |
| 2-Methyl-pentane | 107-83-5 | 0.103 | GC/MS |
| 3-methyl-pentane | 96-14-0 | 0.085 | GC/MS |
| Ethyl acetate | 141-78-6 | 0.261 | GC/MS |
| Hexane | 110-54-3 | 0.109 | GC/MS |
| 2-Methyl-1-propanol | 78-83-1 | 0.139 | GC/MS |
| 3-Methyl-1-butanol | 123-51-3 | 1.082 | GC/MS |
| 2-Methyl-1-butanol | 137-32-6 | 0.511 | GC/MS |
| Hexanal | 66-25-1 | 0.046 | GC/MS |

The analytical values are mean values of two determinations

From the listed components it can be an option to use the bio ethanol obtained by the process to generate heat for the process e.g. by catalytic combustion, and at the same time get rid of polluting volatile organic compounds e.g. hexane.

Example 3

Fermentation in a Batch Process of a Biomass Comprising Polysaccharides and Proteins From a Mixture of Pulses and Cereals Added Various Enzymes as Processing Aid In the following the fermentation of a biomass based on a mixture of defatted soy and wheat is illustrated.

300 kg of a mixture containing 10% by weight of dry matter of crushed wheat and 90% by weight of dry matter of dehulled and defatted, flash desolventised soy flakes were fed to a closed single bladed worm conveyer able to transport, lift and mix the material (bioreactor). At the same time water and a slurry of spent brewer's yeast (10% dry matter) and enzymes where added in an amount to reach a dry matter content of 45% by weight in the mixture.

The fermenting mixture had a content of 3.5% by weight of yeast based on total dry matter and 0.4% by weight based on dry matter of each of Viscozyme Wheat, Spirizyme Fuel and Liquozyme from Novozymes, which enzymes provide alfa-amylase, glucoamylase, beta-glucanase activities and side activities in the form of xylanase and cellulase activities.

In the bioreactor the resulting slurry was transported, mixed and incubated for 18 hours at 34° C.

The ethanol content in the ferment was 73.1 g/kg dry matter corresponding to 7.3 kg per 100 kg dry matter of the wheat/soy mixture.

The wet solid product was flash dried and milled at an Alpine pin mill.

The dried fermented product had a water content of 6.6% by weight and a protein content of 59.1% by weight.

Example 4

Fermentation in a Laboratory Scale Process of a Biomass Comprising Polysaccharides and Proteins From Soy, Added β-lupulic Acid from Hop as Processing Aid The fermentation was performed on a biomass based on a mixture of defatted soy and 3.5% by weight of yeast and water added in an amount to reach a dry matter content of 48% by weight in the mixture.

To the fermentation mixtures β-lupulic acid from hop was added in various concentrations.

The fermentation was performed in small glass containers at 34° C. for 17 hours followed by heat treatment to stop the fermentation.

After the fermentation was terminated the content of soluble carbohydrates was extracted by stirring a watery suspension slurry of 10% DM for 30 min followed by centrifugation for 10 min at 3000×g.

The watery extracts of the ferment was analyzed for carbohydrate content by the phenol-sulphuric acid method (*Carbohydrate analysis—A practical approach*; IRL Press, Oxford. Ed. M. F. Chaplan & J. F. Kenndy, 1986).

The results obtained are tabulated in the following:

| β-lupulic acid Concentration in ppm | Soluble carbohydrates mg/ml in extract |
| --- | --- |
| 0 | 7.9 |
| 75 | 7.7 |
| 1500 | 7.4 |
| 3000 | 7.1 |

The crude ethanol was not isolated in this experiment. However, the crude ethanol might have been separated from the fermented mixture by conventional methods, and the concentration of ethanol in the resulting condensate determined by conventional methods, e.g. as described in example 1.

From the results it can be seen that the use of β-lupulic acid as processing aid reduce the content of water-soluble carbohydrates in the fermented product i.e. it improve the fermentation process.

Example 5

Fermentation in a Batch Process of a Biomass Comprising Polysaccharides and Proteins from Soy, Added Various Hop Based Processing Aids 250 kg of dehulled and defatted, flash desolventised soy flakes were fed to a closed single bladed worm conveyer able to transport, lift and mix the material (bioreactor). At the same time water and a slurry of spent brewer's yeast (10% dry matter) and hop based processing aids where added in an amount to reach a dry matter content of 45% by weight in the mixture.

The fermenting mixture had a content of 3.5% by weight of yeast based on total dry matter and 3000 ppm of α-, or β-acids, or α+β acids, or iso-α-acids from hop.

In the bioreactor the resulting slurry was transported, mixed and incubated for 16 hours at 34° C.

The wet solid product was flash dried and milled at an Alpine pin mill.

The dried fermented products had a water content of 4.5-5.3% by weight and a protein content of 56.0-56.8% by weight.

Before and after the fermentation was terminated the content of soluble carbohydrates was analyzed on watery extracts of the ferment and on the dried product by the method described in Example 4.

As mentioned in example 4 the crude ethanol was not isolated in this experiment either. However, the crude ethanol might have been separated from the fermented mixture by conventional methods, and the concentration of ethanol in the resulting condensate determined by conventional methods, e.g. as described in example 1.

The results obtained are tabulated in the following:

| Type of processing aid added | Main constituents | Soluble carbohydrates Before fermentation | Soluble carbohydrates After fermentation | Soluble carbohydrates Reduction in mg/ml and in % relative | Soluble carbohydrates In an extract of the dried product |
|---|---|---|---|---|---|
| None | — | 15.4 | 7.4 | 8.0-51.9% | 8.3 |
| Hop $CO_2$-extract | $\beta$ - acids | 13.4 | 5.5 | 7.9-59.0% | 6.3 |
| Hop pellets | $\alpha + \beta$ - acids | 13.6 | 7.4 | 6.2-45.6% | 7.8 |
| Hop EtOH-extract | $\alpha + \beta$ - acids | 18.1 | 10.1 | 8.0-44.2% | 9.3 |
| Hop iso-extract | K salt of iso-$\alpha$- acids | 13.1 | 5.1 | 8.0-61.1% | 5.2 |

From the results it can be seen that by the use of various hop components during fermentation it is possible to modulate the amount of soluble carbohydrates.

The presence of a hop extract where the main constituent is $\beta$-acids as well as an extract where the main constituent is iso-$\alpha$-acids reduced the content of soluble carbohydrates, whereas the combined presence of $\alpha$- and $\beta$-acids tend to preserve the content of soluble carbohydrates relative to the reference without any addition of hop processing aids.

As mentioned in example 4 the crude ethanol was not isolated in this experiment as well. However, the crude ethanol might have been separated from the fermented mixture by conventional methods, and the concentration of ethanol in the resulting condensate determined by conventional methods, e.g. as described in example 1.

The invention claimed is:

1. A method for the simultaneous production of a fermented, solid product and ethanol comprising:
   providing an initial mixture of milled or flaked or otherwise disintegrated biomass, comprising oligosaccharides and/or polysaccharides, and live yeast in a dry matter ratio of from 2:1 to 100:1, and water, wherein the water content in the initial mixture does not exceed 65% by weight of the initial mixture;
   fermenting the initial mixture for 1-36 hours at a temperature of about 25-60° C. under anaerobic conditions to obtain a fermented mixture;
   separating wet fermented, solid product from the fermented mixture; and
   separating crude ethanol from the fermented mixture;
   wherein:
   (a) the fermenting step is performed in one or more interconnected paddle worm or continuous worm conveyers with inlets for the fermentation mixture and additives, an outlet for the ferment, and controls for rotation speed, temperature and pH, or
   (b) one or more processing aids are added prior to the fermenting step, and optionally in the fermenting step.

2. The method according to claim 1, wherein the fermenting step is performed in one or more interconnected paddle worm or continuous worm conveyers with inlets for the fermentation mixture and additives, an outlet for the ferment, and controls for rotation speed, temperature and pH.

3. The method according to claim 2, wherein one or more processing aids are added prior to the fermenting step and/or in the fermenting step.

4. The method according to claim 1, wherein one or more processing aids are added prior to the fermenting step, and optionally in the fermenting step.

5. The method according to claim 4, wherein the fermenting step is performed in a vertical screw mixer or one or more interconnected paddle worm or continuous worm conveyers with inlets for the fermentation mixture and additives, an outlet for the ferment, and controls for rotation speed, temperature and pH.

6. The method according to claim 1, wherein the one or more interconnected paddle worm or continuous worm conveyers is arranged non-vertically.

7. The method according to claim 1, wherein at least one of the one or more processing aids is an enzyme selected from the group consisting of a protease, peptidase, $\alpha$-galactosidase, amylase, glucanase, pectinase, hemicellulase, phytase, lipase, phospholipase and oxido-reductase, and wherein an enzymatic saccharification process converting said oligosaccharides and/or polysaccharides into fermentable carbohydrates takes place in the fermenting step.

8. The method according to claim 1, wherein at least one of the one or more processing aids is a plant-based component selected from the group consisting of rosemary, thyme, oregano, flavonoids, phenolic acids, saponins and $\alpha$- and $\beta$-acids from hops.

9. The method according to claim 7, wherein at least one of the one or more processing aids is $\alpha$-galactosidase.

10. The method according to claim 1, further comprising, after the fermenting step:
    further fermenting the mixture resulting from the fermenting step for 1-36 hours at a temperature of about 25-60° C. under aerobic conditions, and optionally separating crude ethanol from the fermented mixture thereby obtained.

11. The method according to claim 1, where the continuous worm conveyer is a modified type of a single bladed or multi bladed Archimedean screw or intersected screw, designed to transport the fermenting mixture in a non-vertical direction and at the same time lifting the material so that it is transported and agitated without compacting it.

12. The method according to claim 1, wherein the live yeast is selected from the group consisting of *Saccharomyces cerevisiae* strains, spent brewer's yeast, spent distiller's yeast, spent yeast from wine production, and yeast strains fermenting C5 sugars.

13. The method according to claim 1, where the biomass comprising oligosaccharides and/or polysaccharides further comprises proteins originating from proteinaceous plant parts of a plant selected from the group consisting of soy, pea, lupine, and/or cereals.

14. The method according to claim 13, where said biomass comprises proteins originating from wheat.

15. The method according to claim 1, where the biomass comprising oligosaccharides and/or polysaccharides and optionally proteins further comprises oils and fats from seeds of oil bearing plants.

16. The method according to claim 15, where said biomass comprises oils and fats from rapeseed.

17. The method according to claim 1, performed as a batch, fed-batch or continuous process.

18. The method according to claim 1, wherein the fermenting step is performed under conditions where the water content in the initial mixture does not exceed 60%.

19. The method according to claim 1, wherein the fermenting step is performed under conditions where the water content in the initial mixture does not exceed 55%.

20. The method according to claim 1, wherein the fermenting step is performed under conditions where the water content in the initial mixture does not exceed 50%.

21. The method according to claim 1, wherein the fermenting step is performed under conditions where the water content in the initial mixture does not exceed 45%.

* * * * *